United States Patent [19]

Sharma

[11] Patent Number: 5,021,454
[45] Date of Patent: Jun. 4, 1991

[54] BENZOYLAMINOALKANOIC ACIDS AND ESTERS

[75] Inventor: Ashok K. Sharma, Perkasie, Pa.

[73] Assignee: Rohm and Haas Company, Philadelphia, Pa.

[21] Appl. No.: 418,063

[22] Filed: Oct. 6, 1989

[51] Int. Cl.[5] ............................................. A01N 37/12
[52] U.S. Cl. ..................................... 514/541; 514/514; 514/516; 514/521; 514/522; 514/563; 558/11; 558/12; 558/392; 558/415; 560/22; 560/39; 560/41; 562/437; 562/444; 562/449
[58] Field of Search ............... 560/41, 72, 39; 558/11, 558/12, 392, 415; 562/437, 444, 449; 514/514, 516, 521, 517, 541, 563

[56] References Cited

U.S. PATENT DOCUMENTS

| | | | |
|---|---|---|---|
| 3,661,991 | 5/1972 | McNulty et al. | 260/558 D |
| 3,751,239 | 8/1973 | McNulty et al. | 71/118 |
| 3,880,903 | 4/1975 | Rohr et al. | 560/41 |
| 4,822,902 | 4/1989 | Carley et al. | 558/14 |
| 4,863,940 | 9/1989 | Sharma | 514/359 |

OTHER PUBLICATIONS

Elmoghayar, *Chemical Abstracts,* vol. 99, No. 105188q (1983).

*Primary Examiner*—Bruce Gray
*Attorney, Agent, or Firm*—Barbara V. Maurer

[57] ABSTRACT

Benzoylaminoalkanoic acids and esters thereof are fungitoxic and useful for controlling fungi, particularly phytopathogenic fungi.

14 Claims, No Drawings

BENZOYLAMINOALKANOIC ACIDS AND ESTERS

This invention relates to benzoylaminoalkanoic acids and esters, compositions containing these compounds and a method of controlling phytopathogenic fungi by the use of a fungitoxic amount of these compounds.

BACKGROUND OF THE INVENTION

N-(1,1-dialkyl-3-chloroacetonyl) substituted benzamides are known to have fungicidal activity. See, for example, U.S. Pat. Nos. 3,661,991 and 3,751,239 which disclose a terminal carbon of the acetonyl group as only substituted by chloro or hydrogen atoms.

The compounds of the present invention relate to a different class of compounds.

DESCRIPTION OF INVENTION

The present invention is a class of benzoylaminoalkanoic acid and ester compounds of the formula (I):

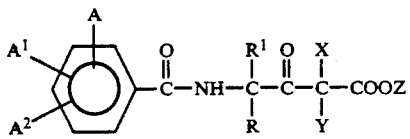

wherein

A, $A^1$ and $A^2$ are each independently selected from hydrogen, halogen, $(C_1-C_4)$alkyl, halo$(C_1-C_3)$alkyl, $(C_1-C_4)$alkoxy, halo$(C_1-C_3)$alkoxy, cyano, nitro, phenyl, phenyl$(C_1-C_3)$alkyl or phenyloxy;

R and $R^1$ are each independently selected from hydrogen, $(C_1-C_6)$alkyl, phenyl, phenyl$(C_1-C_4)$alkyl and halo$(C_1-C_3)$alkyl;

X is halogen, cyano or thiocyano (—SCN);

Y is hydrogen, halogen, cyano or thiocyano; and

Z is hydrogen, $(C_1-C_8)$alkyl, $(C_1-C_3)$alkoxy, $(C_1-C_3)$alkyl, halo$(C_1-C_8)$alkyl, phenyl, phenyl$(C_1-C_4)$alkyl, phenoxy$(C_1-C_4)$alkyl, $(C_1-C_4)$alkoxycarbonyl$(C_1-C_4)$alkyl, acyl$(C_1-C_6)$alkyl or thio$(C_1-C_8)$alkyl; and the agronomically acceptable salts thereof.

Alkyl, either by itself or as part of any substituent listed above, means straight and branched alkyl groups, for example, methyl, ethyl, isopropyl and hexyl. Haloalkyl means alkyl substituted with one or more halogen atoms, for example, chloroethyl, chloromethyl or trifluoromethyl. Haloalkoxy means alkoxy substituted with one or more halogen atoms. Phenylalkyl is, for example, benzyl or phenethyl. Alkoxycarbonylalkyl is, for example, ethoxycarbonylmethyl. Alkoxyalkyl is, for example, methoxyethyl or methoxymethyl.

Halogen means fluorine, chlorine, bromine and iodine.

Phenyl, either by itself or as part of any substituent listed above, is unsubstituted or substituted by from one to three groups independently selected from $(C_1-C_4)$alkyl, fluorine, chlorine, bromine, nitro, $(C_1-C_3)$alkoxy and halo$(C_1-C_3)$alkyl. Preferably, when A is phenyl, phenoxy or phenylalkyl, neither $A^1$ or $A^2$ is phenyl, phenoxy or phenylalkyl.

Agronomically acceptable salts include those known in the art, for example, metal salts such as sodium, potassium, calcium and magnesium.

In a preferred embodiment of the invention, A is hydrogen, chloro, bromo, fluoro, iodo, trifluoromethyl, trifluoromethoxy, methyl, ethyl, phenyl, methoxy, chloromethyl or cyano; $A^1$ and $A^2$ are each independently selected from hydrogen, chloro, bromo, fluoro, and methyl groups; R and $R^1$ are hydrogen, $(C_1-C_6)$alkyl or phen$(C_1-C_2)$alkyl; X is fluoro, chloro, bromo or thiocyano; Y is hydrogen, fluoro, chloro, bromo or thiocyano; and Z is hydrogen, $(C_1-C_5)$alkyl, halo$(C_1-C_5)$alkyl having from 2 to 6 halogens, phenyl, $(C_1-C_3)$alkoxy$(C_1-C_3)$alkyl, $(C_1-C_3)$alkoxycarbonyl$(C_1-C_3)$alkyl, or phenyl$(C_2-C_4)$alkyl and the agronomically acceptable salts thereof.

More preferably, A, $A^1$ and $A^2$ are at the 3-, 4- or 5-position of the phenyl ring; A is chloro, bromo, trifluoromethyl, fluoro or methyl; $A^1$ and $A^2$ are each independently selected from hydrogen, chloro, bromo and fluoro; R and $R^1$ are each independently $(C_1-C_4)$alkyl; X is bromo or chloro; Y is hydrogen, fluoro, chloro or bromo; and Z is hydrogen, $(C_1-C_3)$alkyl, $(C_1-C_3)$alkoxy$(C_1-C_3)$alkyl, halo$(C_2-C_4)$alkyl having from 1 to 4 halogens, phenyl, halophenyl or $(C_1-C_3)$alkoxycarbonyl $(C_1-C_3)$alkyl.

Particularly preferred compounds of the invention are those wherein A, $A^1$ and $A^2$ are at the 3-, 4- and 5-positions respectively of the phenyl ring; A is chloro, bromo, fluoro, trifluoromethyl or methyl group; $A^1$ is hydrogen; $A^2$ is hydrogen, chloro, bromo or fluoro; R and $R^1$ are each independently $(C_1-C_2)$alkyl; X is Br or Cl; Y is hydrogen or chloro; and Z is hydrogen, methyl, ethyl, chloroethyl, chlorophenyl, methoxyethyl or ethoxycarbonylmethyl.

The benzoylaminoalkanoic acids and esters can be prepared by known synthesis methods. For example, the compounds can be synthesized from N-propynylamides (4) which are prepared according to Scheme I.

SCHEME I

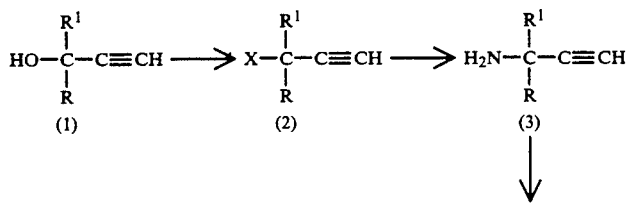

SCHEME I

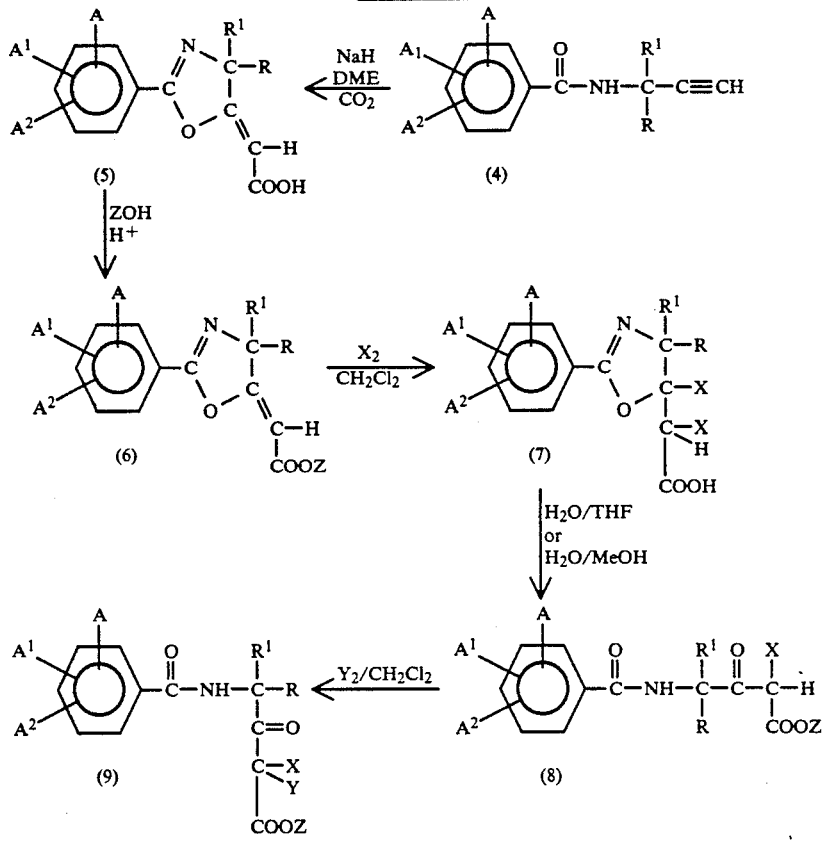

Thus, a propargyllic alcohol (1), wherein R and $R^1$ are as defined for Formula I, is converted to its chloride or p-toluenesulfonate (2) (wherein X is Cl or p-toluenesulfonyl) by methods described in the literature, then treated with sodium in liquid ammonia at a temperature from about $-50°$ C. to about $-30°$ C. to give the corresponding propargyllic amine (3). The amine (3) is reacted at from about $-10°$ C. to about room temperature with an equimolar amount of an acid halide in a solvent in the presence of one equivalent of a base such as pyridine, triethylamine, sodium hydroxide or potassium hydroxide to produce an N-propylnyl-benzamide (4). Examples of solvents include ether, chloroform, toluene, glyme, tetrahydrofuran, hexene, ethyl acetate and water. Alternatively, the amine (3) can be reacted with an equimolar amount of a carboxylic acid such as benzoic acid activated by a reagent such as dicyclohexylcarbodiimide, methane- sulfonyl chloride, or 6-chloro-N-methylpyridinium chloride to obtain the N-propynylbenzamide (4).

The N-propynylamide (4) is treated with a strong base such as 2 to 3 equivalents of sodium or potassium hydride in dimethylformamide (DMF), dimethoxyethane (DME), or dimethylsulfoxide (DMSO), then reacted at from about $-10°$ C. to about $20°$ C. with a large excess of carbon dioxide which is bubbled into the reaction mixture. The resulting mixture is subsequently neutralized with an acid such as hydrochloric acid, sulfuric acid, phosphoric acid, acetic acid or nitric acid, typically as a 10% aqueous solution, to obtain the corresponding oxazoline acid (5). The acid is esterified (when Z is H) with a desired alcohol in the presence of thionyl chloride to produce ester (6). The ester (6) is then halogenated by treating it with a halogen source $(X_2)$, for example, chlorine, bromine, or trifluoromethylhypofluorite at a temperature of from about $-30°$ C. to about $100°$ C. and preferably at a temperature of from about $0°$ to about $20°$ C. in the presence of a hydrocarbon or halogenated hydrocarbon solvent such as methylene chloride, chloroform, or carbon tetrachloride.

Alternatively, the acid (5) may be esterified using a diazo compound such as diazomethane or ethyl diazoacetate; or by reacting the acid with an appropriate alcohol in the presence of an activating agent such as triphenylphosphine-diethylacetylenedicarboxylate or 6-chloro-1-methylpyridinium chloride. These methods have been reported in the literature for the preparation of esters.

When Z is alkoxycarbonylalkyl, the diazo compound method is required, and the reaction is catalyzed by copper powder.

Compounds of structure (7) may be hydrolyzed to obtain the compounds of structure (8). This hydrolysis is accomplished by stirring the compound (7) at from about $20°$ C. to about $50°$ C. in wet solvent such as water/THF or water/alcohol.

Compounds of structure (9) where X and Y are not hydrogen are prepared from compound (8, X,Y=H) by reacting (8) with an excess halogenating agent such as chlorine, bromine, N-chlorosuccinimide (NCS), N-bromosuccinimide (NBS), or $CF_3OF$, in a halogenated hydrocarbon solvent such as $CH_2Cl_2$, $CHCl_3$, or $CCl_4$ at temperature of from about $-60°$ C. to about $70°$ C.

When X is halogen and Z is hydrogen, the compound (5) may be halogenated with the previously described halogenating agents and by the same general methods, and then hydrolysed as described above to obtain the desired products.

When X and/or Y substituents of desired benzoylamine compound are a cyano and/or thiocyano group, then these groups are introduced by the nucleophilic displacement of the halogen atom(s) of (7) by an alkali metal cyanide or thiocyanate. The desired benzoylaminoalkanoic ester is obtained by hydrolyzing compound (7) under neutral or acidic conditions using an acid such as hydrochloric, hydrobromic or sulfuric acid and a solvent such as water, methanol, ethanol, isopropanol, tetrahydrofuran (THF), dioxane, acetic acid or dimethylsulfoxide at a temperature of from about 10° C. to about 100° C., preferably at about 35° C. to about 50° C. to obtain the desired product (8).

The following compounds listed in Table 1 are meant to be non-limiting and illustrative of the invention. Proton magnetic resonance data for the compounds are listed in Table 2. Illustrative preparations of the compounds are described after Table II.

TABLE 1

[Structure: 3-chloro, A² substituted phenyl—C(=O)—NH—C(R)(CH₃)—C(=O)—C(X)(Y)—COOZ]

| Example | A² | R | X | Y | Z |
|---|---|---|---|---|---|
| 1 | Cl | CH₃ | Cl | H | CH₃ |
| 2 | Cl | CH₃ | Cl | H | C₂H₅ |
| 3 | Cl | CH₃ | Cl | H | C₆H₄-4-Cl |
| 4 | Cl | CH₃ | Cl | H | H |
| 5 | Cl | CH₃ | Cl | H | i-Pr |
| 6 | Cl | CH₃ | Cl | H | CH₂CH₂Cl |
| 7 | Cl | CH₃ | Br | H | CH₃ |
| 8 | Cl | CH₃ | Br | H | H |
| 9 | Cl | CH₃ | Br | H | C₂H₅ |
| 10 | Cl | CH₃ | Br | H | C₆H₄-4-Cl |
| 11 | Cl | CH₃ | Br | H | Na |
| 12 | Cl | C₂H₅ | Cl | H | CH₃ |
| 13 | Cl | C₂H₅ | Br | H | CH₃ |
| 14 | Cl | C₂H₅ | Cl | H | H |
| 15 | Cl | C₂H₅ | Br | H | H |
| 16 | H | C₂H₅ | Br | H | H |
| 17 | H | C₂H₅ | Cl | H | CH₃ |
| 18 | Cl | CH₃ | Cl | H | CH₂CH₂OCH₃ |
| 19 | Cl | CH₃ | Cl | H | CH₂COOC₂H₅ |
| 20 | Cl | C₂H₅ | Cl | Cl | CH₃ |
| 21 | Cl | CH₃ | H | H | H |

TABLE 2

¹H-NMR SPECTRA

| Compound Number | Solvent | 200 MHz, delta scale in ppm, TMS standard |
|---|---|---|
| 1 | CDCl₃ | 7.6, m, 2H; 7.5, m, 1H; 7.2, br, 1H; 5.4, s, 1H; 3.9, s, 3H; 1.9, two s, 6H. |
| 2 | CDCl₃ | 7.7, m, 2H; 7.5, m, 1H; 7.25, br, 1H; 5.5, s, 1H; 4.5–4.1, q, 2H; 1.6, two s, 6H; 1.4–1.1, t, 3H. |
| 3 | CDCl₃ | 7.5, m, 2H; 7.3, m, 1H; 7.3–6.8, ABq & br, 5H; 5.4, s, 1H; 1.6, two s, 6H. |
| 4 | acetone-d₆ | 9.5, br, 1H; 8.3, br, 1H; 7.9, m, 2H; 7.6, m, 1H; 6.9, s, 1H; 1.7, s, 6H. |
| 5 | CDCl₃ | 7.6, m, 2H; 7.5, m, 1H; 5.4, s, 1H; 5.4–4.9, m, 1H; 1.8, s, 6H; 1.4, m, 6H. |
| 6 | CDCl₃ | 8.2, br, 1H; 7.6, m, 2H; 7.2, m, 1H; 5.3, s, 1H; 4.4, t, 2H; 3.6, t, 2H; 1.6, two s, 6H. |
| 7 | CDCl₃ | 7.8, m, 2H; 7.7, m, 1H; 7.2, br, 1H; 5.4, s, 1H; 3.95, s, 3H; 1.9, s, 6H. |
| 8 | acetone-d₆ | 9.5, br, 1H; 7.8, m, 2H; 7.4, m, 1H; 6.45, s, 1H; 1.6, s, 6H. |
| 9 | CDCl₃ | 7.7, m, 2H; 7.5, m, 1H; 7.25, br, 1H; 5.5, 5, 1H; 4.5–4.1, q, 2H; 1.6, two s, 6H; 1.4–1.1, t, 3H. |
| 10 | CDCl₃ | 7.8, m, 2H; 7.4, m, 1H; 7.4–6.9, ABq & br, 5H; 5.5, s, 1H; 1.6, two s, 6H. |
| 12 | CDCl₃ | 7.6, m, 2H; 7.5, m, 1H; 6.9, br, 1H; 5.35, m, 1H; 3.8, s, 3H; 2.5–2.0, q, 2H; 1.76, s, 3H; 1.1–0.8, t, 3H. |
| 13 | CDCl₃ | 7.6, m, 2H; 7.5, m, 1H; 6.9, br, 1H; 5.4, m, 1H; 3.8, s, 3H; 2.4–1.95, q, 2H; 1.7, s, 3H; 1.1–0.7, t, 3H. |
| 14 | CDCl₃ | 8.8–8.5, br, 1H; 7.9–7.3, m, 4H; 6.45, s, 1H; 2.2–1.9, q, 2H; 1.3, s, 3H; 1.05–0.75, t, 3H. |
| 15 | CDCl₃ | 8.5–8.1, br, 1H; 7.6, m, 2H; 7.3, m, 1H; 7.15–6.8, br, 1H; 6.2, s, 1H; 2.2–2.0, q, 2H; 1.75, s, 3H; 1.0–0.75, t, 3H. |
| 16 | CDCl₃ | 9.5, br, 1H; 8.0–7.4, m, 5H, 5.4, two s, 1H; 2.4–2.1, q, 2H; 1.6, two s, 3H; 1.2–0.9, t, 3H. |
| 17 | CDCl₃ | 7.8–7.2, m, 4H; 6.8, br, 1H; 5.3, s, 1H; 3.8, s, 3H; 2.5–2.0, m, 2H; 1.8, s, 3H; 1.1–0.8, t, 3H. |
| 18 | CDCl₃ | 7.6, m, 2H; 7.45, m, 1H; 6.9, br, 1H; 5.5, s, 1H; 4.4, t, 2H; 3.65, t, 2H; 3.4, s, 3H; 1.65, two s, 6H. |
| 19 | CDCl₃ | 7.7, br, 1H; 7.6, d, 2H; 7.4, t, 1H; 5.5, s, 1H; 4.7, s, 2H; 4.4–4.05, q, 2H; 1.75 & 1.65, two s, 6H; 1.4–1.2, t, 3H. |
| 20 | CDCl₃ | 7.6, m, 2H; 7.5, m, 1H; 7.1, br, 1H; 4.0, s, 3H, 2.5–2.1, t, 2H; 1.85, s, 3H; 1.2–0.9, t, 3H. |
| 21 | CDCl₃ | 8.5, br, 1H; 7.9, d, 1H; 7.55, t, 1H; 7.6, br, 1H; 5.3, s, 2H, 1.6, s, 6H. |

EXAMPLE 1

2-Chloro-4-(3,5-dichlorobenzoylamino)-4-methyl-3-oxopentanoic acid, methylester (Compound 1)

a.

2-(3,5-Dichlorophenyl)-4,4-dimethyl-5(4H)-oxazolydeneacetic acid

N-(1,1-Dimethylpropyn-3-yl)-3,5-dichlorobenzamide (25.6 grams (g), 0.1 mol) was dissolved in dry dimethoxyethane under a nitrogen atmosphere. Sodium hydride (4.8 g of 60%, 0.12 mol) was added in portions with stirring at room temperature. An exothermic reaction with hydrogen evolution was observed. When the hydrogen evolution ceased, carbon dioxide was bubbled into the reaction mixture, and the reaction progress was monitored by thin layer chromatography. After 6 hours, the reaction was quenched with 5% aqueous sodium hydroxide and the solids were filtered out. The filtrate was acidified with 5% aqueous hydrochloric acid to yield a white solid which was collected by filtration and dried to yield 11.0 gm of product (37%).

b.

2-(3,5-Dichlorophenyl)-4,4-dimethyl-5-(4H)-3-oxazolydeneacetic acid, methyl ester The acid prepared in step 1a (3.0 g, 0.01 mol) was taken up in methanol (75 ml) and thionyl chloride (3.7 ml, 0.05 mol) was added slowly with stirring. An exothermic reaction occurred and the temperature rose to 40° C. The reaction mixture was stirred for a half hour while maintained at a temperature of about 40°–50° C. Then the solvent was removed in vacuo and the residue slurried in ether and hexane (1:5) to yield 3.0 g of white solid product (95.5%).

c.
2-Chloro-4-(3,5-dichlorobenzoylamino)-4-methyl-3-oxopentanoic acid, methyl ester The methyl ester prepared in Step 1b (2.6 g, 0.0083 mol) was dissolved in methylene chloride (200 ml) and chlorine gas was bubbled into this solution until light yellow color persisted (about 60 seconds), and stirred for about another 30 minutes. The volatiles were evaporated in vacuo and the residue redissolved in methanol (50 ml). Enough water was added to obtain a turbid solution and then stirred at room temperature after adding concentrated hydrochloric acid (2 ml). After 16 hours, the reaction mixture was poured into ice water (400 ml). The white solid was filtered and dried. After recrystallization from ether and hexane (1:5), 2.1 g (70%) of product were obtained.

Compounds 2, 5, 6, 7, 9, 12, 13, 17 and 18 were prepared according to the same procedure using the appropriate reagents.

Compounds 4, 8, 14, 15 and 16 were prepared by taking the acid from step 1a and carrying it directly onto step 1c. The chlorination or bromination, step 1c, required a longer amount of time (1-6 hours).

Compound 11 was prepared from compound 8 by means known in the art.

Compound 21 was prepared by hydrolyzing the product from Step 1a in tetrahydrofuran/water (50:50 v/v) at room temperature for 16 hours.

EXAMPLE 2

2-Chloro-4-(3,5-dichlorobenzoylamino)-4-methyl-3-oxopentanoic acid, 2-ethoxy-2-oxoethyl ester (Compound 19)

a.
2-(3,5-Dichlorophenyl)-4,4-dimethyl-5(4H)-oxazolydeneacetic acid, 2-ethoxy-2-oxoethyl ester 2-(3,5-Dichlorophenyl)-4,4-dimethyl-5(4H)-oxazolydeneacetic acid (6.0 g, 0.02 mol) was placed in a 100 ml three neck flask under nitrogen along with copper powder (200 mg). Ethyl diazoacetate (2.4 g, 0.02 mol) was added gradually, and the mixture stirred overnight. An additional 5 g of ethyl diazoacetate was added with cooling, and stirred the mixture for another 4 hours. At this point, all of the acid starting material had dissolved. The solution was filtered through a short bed of silica gel and Celite ®, and the filtrate was evaporated in vacuo. The residual oily material was distilled under vacuum and the material distilling at 40° to 50° C. (1 mm) was removed. The residue was 2-(3,5-dichlorophenyl)-4,4-dimethyl-5(4H)-oxazolydene-acetic acid, 2-ethoxy-2-oxoethyl ester.

b.
2-Chloro-4-(3,5-dichlorobenzoylamino)-4-methyl-3-oxopentanoic acid, 2-ethoxy-2-oxoethyl ester The product obtained above was chlorinated with chlorine (in 2 equivalents) in methylene chloride for 1 hour at room temperature and then hydrolysed in water-THF (50 ml, 1:1) at 50° C. for 12 hours. The resulting solution was transferred to a separatory funnel with the aid of ether (100 ml), and the organic layer was washed with water, saturated sodium bicarbonate, and brine. Drying of the ether solution followed by solvent removal in vacuo gave 6.5 gm of the crude expected product (~90% pure). Purification by column chromatography over silica gel and using ether-hexane (1:4) as eluent yielded 3.6 gm pure product.

EXAMPLE 3

2-Chloro-4-(3,5-dichlorobenzoylamino)-4-methyl-3-oxopentanoic acid, 4-chlorophenyl ester (Compound 3); and
2-Bromo-4-(3,5-dichlorobenzoylamino)-4-methyl-3-oxopentanoic acid, 4-chlorophenyl ester (Compound 10)

2-(3,5-Dichlorophenyl)-4,4-dimethyl-5(4H)-oxazolydene-acetic acid (20 g, 0.0666 mol, prepared as shown in Example 1a) was taken in a 100 ml round bottom flask in methylene chloride (MDC, 40 ml) under nitrogen atmosphere. Thionyl chloride (30 ml, 49 g, 0.41 mol) was added gradually over 30 min. After evolution of gas ceased, a clear yellow solution was obtained, which was stirred at room temperature overnight. The volatiles were removed under reduced pressure, and the resulting yellow paste was slurried in hexane to afford a light yellow solid which was filtered quickly and stored in a tightly closed bottle. 2-(3,5-Dichlorophenyl)-4,4-dimethyl-5(4H)-oxazolydeneacetic acid chloride (22 gm) was recovered.

The acid chloride (5.0 g) was taken in dry ether (50 ml) under nitrogen, and sodium salt of 4-chlorophenol (2.8 g) was added in one portion with stirring. This mixture was allowed to stir overnight and then filtered. The clear solution thus obtained was divided into two equal portions.

One portion was chlorinated and then hydrolyzed according to the procedure described in Example 1b and c, to obtain 2-chloro-4-(3,5-dichlorobenzoylamino)-4-methyl-3-oxopentanoic acid, 4-chlorophenyl ester (Compound 3).

The other portion was similarly brominated and hydrolyzed to obtain 2-bromo-4-(3,5-dichlorobenzoylamino)-4-methyl-3-oxopentanoic acid, 4-chlorophenyl ester (Compound 10).

EXAMPLE 4

2,2-Dichloro-4-(3,5-dichlorobenzoylamino)-4-methyl-3-oxohexanoic acid, methyl ester (Compound 20)

Compound 12 (5.0 g), prepared by the method described in Example 1, in methylene chloride (100 ml) was placed in a round bottom flask equipped with magnetic stirrer. Chlorine gas was bubbled into the solution until the solution turned yellow and it was allowed to stir at room temperature. The process of bubbling in chlorine gas was repeated several times at ½ hour intervals until no starting material remained (TLC). The solvent was then evaporated from the reaction mixture in vacuo to yield 5.2 g product which was recrystallized from ether/hexane to yield 3.1 g of pure product.

The compounds of the present invention have fungitoxic activity, particularly against phytopathogenic fungi. They are active against fungi of a number of classes including Deuteromycetes (*Fungi Imperfecti*), Basidiomycetes, Ascomycetes and Phycomycetes. Genera against fungi which the present compounds may be used include Colletotrichum, Piricularia, Puccinia, Erysiphe, Pseudoperonospora, Plasmopara and Phytophthora which include such diseases as cucumber anthracnose, rice blast, wheat stem and leaf rust, powdery mildews, downy mildews, tomato late blight, potato late blight and pepper blight.

The compounds of the present invention are particularly useful for the control of Phycomycetes fungi which cause late blights in potatoes and tomatoes and downy mildews in grapes, cucumbers, squash, melons, broccoli and other cole crops. Examples of Phycomycetes fungi include *Pseudoperonospora cubensis, Plasmopara viticola, Phytophthora infestans,* and *Phytophthora capsici* (potato late blight).

The benzoylamino compounds of the invention can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled, but the effective amount is usually from about 0.01 kilogram (kg) to about 20 kg, preferably from about 0.1 to about 5 kg and more preferably from about 0.125 to about 0.5 kg of active ingredient per hectare.

As a seed protectant, the amount of toxicant coated on the seed is usually at a dosage rate of about 10 to about 250 grams (g) and preferably from about 20 to about 60 g per 40 kilograms of seed. As a soil fungicide, the chemical can be incorporated in the soil or applied to the surface usually at a rate of 0.5 to about 20 kg and preferably about 1 to about 5 kg per hectare. As a foliar fungicide, the benzoylamino derivatives are usually applied to growing plants at a rate of about 0.1 to about 5 and preferably from about 0.125 to about 0.5 kg per hectare.

The compounds of the present invention are useful for the control of fungi and can be utilized at various loci such as the seed, the soil or the foliage. For such purposes, these compounds can be used in the technical or pure form as prepared, as solutions or as formulations. The compounds are usually taken up in a carrier or are formulated so as to render them suitable for subsequent use of fungicides. For example, these chemical agents can be formulated as wettable powders, dry powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly, in the case of foliar spray formulations, to include adjuvants, such as wetting agents, spreading agents, dispersing agents, stickers, adhesive and the like in accordance with agricultural practices. Such adjuvants commonly used in the art can be found in *McCutcheon's Emulsifiers and Detergents, McCutcheon's Emulsifiers and Detergents/Functional Materials* and *McCutcheon's Functional Materials* all published annually by McCutcheon Division of MC Publishing Company (New Jersey).

In general, the compounds utilized in this invention can be dissolved in appropriate solvents such as acetone, methanol, ethanol, dimethylformamide or dimethyl sulfoxide and such solutions extended with water. The concentrations of the solution can vary from 1 to 90% with a preferred range being 5 to 50%.

For the preparation of emulsifiable concentrates, the compounds of the invention can be dissolved in suitable organic solvents or a mixture of solvents, together with an emulsifying agent which permits dispersion of the fungicide in water. The concentration of the active ingredient in emulsifiable concentrates is usually 10 to 90%, and in flowable emulsion concentrates, this can be as high as 75%.

Wettable powders, suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20 to 98%, preferably 40 to 75%. A typical wettable powder is made by blending 50 parts of 2-chloro-4-(3,5-dichlorobenzoylamino)-4-methyl-3-oxo-hexanoic acid, methyl ester, 45 parts of a synthetic precipitated hydrated silicon dioxide sold under the trademark Hi-Sil ® and 5 parts of sodium lignosulfonate (Marasperse ® N-22). In another preparation of a kaolin type, (Barden) clay is used in place of the Hi-Sil in the above-wettable powder, and in another such preparation, 25% of the Hi-Sil is replaced with a synthetic sodium silico aluminate sold under the trademark Zeolex ® 7.

Dusts are prepared by mixing the benzoylaminoalkanoic acid and salts and derivatives thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing 20 to 80% of the active ingredient are commonly made and are subsequently diluted to 1 to 10% use concentration.

The compounds of the present invention may be utilized in combination with other fungicides such as:

(a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl-3,3-dimethylacrylate (binapacryl), and 2-sec-butyl-4,6-dinitrophenyl isopropyl carbonate;

(c) heterocyclic structures such as: N-trichloromethyl-thiotetrahydrophthalimide (captan), N-trichloromethyl-thiophthalimide (folpet), 2-heptadecyl-2-imidazole acetate (glyodine), 2-octylisothiazolone-3,2,4-dichloro-6-(o-chloroanilino)-s-triazine, diethyl phthalimidophosphorothioate, 4-butyl-1,2,4-triazole, 5-amino-1-[bis-(dimethylamino)-phosphinyl]-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-[4,5-b]quinoxaline-2-thione (thioquinox), methyl 1-(butylcarbamoyl)-2-benzimidazole carbamate (benomyl), 2-4'-(thiazolyl)benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinclozolin); 3-(3,5-dichlorophenyl)-N-(1-methylethyl)-2,4-dioxo-1-imidazolidinecarboxamide (iprodione); N-(3,5-dichlorophenyl)-1,2-dimethylcyclopropane-1,2-dicarboximide (procymidone); beta-(4-chloro-phenyloxy)-alpha-(1,1- dimethylethyl)-1H-1,2,4-triazole-1-ethanol (triadimenol); 1-(4-chlorophenoxy)-3,3-dimethyl-1-(1H-1,2,4-triazol-1-yl)-2-butanone (triadimefon); beta-[(1,1'-biphenyl)-4-yloxy]-alpha-(1,1-dimethylethyl)-1H-1,2,4-triazole-1-ethanol (bitertanol); 2,3-dichloro-N-(4-fluorophenyl) maleimide (fluoroimide); 1-[2-(2,4-dichlorophenyl)-4-propyl-1,3-dioxolan-2-ylmethyl]-1H-1,2,4-triazole; pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, alpha-(phenyl)-alpha-(2,4-dichlorophenyl)-5-pyrimidinylmethanol (triarimol), cis-N-[(1,1,2,2-tetrachloroethyl)thio]-4-cyclohexene-1,2-dicarboximide, 3-[2-(3,5-dimethyl-2-oxycyclohexyl-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethyl-amino-4-hydroxy-6-methyl-pyrimidine (ethirimol), acetate of 4-cyclodeceyl-2,6-dimethylmorpholine (dodemorph), and 6-methyl-2-oxo-1,3-dithiolo-[4,5-b]-quinoxaline (quinomethionate);

(d) miscellaneous halogenated fungicides such as: tetrachloro-p-benzoquinone (chloranil), 2-3-dichloro-1,4-napththoquinone (dichlone), 1,4-dichloro-2,5-dimethoxybenzene (chloroneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: copper hydroxide, cuprous oxide, basic cupric chloride, basic copper carbonate, copper terphthalate, copper napthenate and Bordeaux mixture; and (g) miscellaneous fungicides such as: diphenyl sulfone, dodecylguanidine acetate (dodine), phenylmercuric acetate, N-ethyl-mercuri-1,2,3,6-tetrahydro-3,6-endomethano-3,4,5,6,7,7-hexachlorophthalimide, phenyl-mercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, 1,2-bis(3-methoxycarbonyl-2-thio-ureido) benzene (thiophanatemethyl).

It is particularly advantageous to utilize the present invention in combination with a dithiocarbamate, e.g., mancozeb or maneb, for added control of non-Phycomycetes fungi.

The compounds of Examples 1-21 were tested for their fungicidal activity. The compounds were tested in vivo against cucumber downy mildew (*Pseudoperonospora cubensis*) and tomato late blight (*Phytophthora infestans*) and in vitro against Pythium damping off (*Pythium ultimum*) and pepper blight (*Phytophthora capsici*).

(a) Cucumber Downy Mildew (CDM)

*Pseudoperonospora cubensis* was maintained on leaves of live cucumber plants in a constant temperature room at about 65° to 75° F. in humid air with moderate light intensity for 7 to 8 days. A water suspension of the spores from infested leaves was obtained and the spore concentration was adjusted to about $1 \times 10^5$ spores per milliliter (ml).

Marketer cucumber seedlings were selected at their one to two true leaf stage and thinned to one plant (or two leaves) per pot. The seedlings were sprayed to runoff with a solution of a test compound comprising 300 ppm of the active ingredient of the test compound in a 2:1:1 mixture of water, acetone and methanol. After drying, a spore suspension of cucumber downy mildew was applied to the lower surface of the plant leaves with a DeVilbiss atomizer until finer droplets were visible on the leaves. The inoculated seedlings were placed in a humidity cabinet for 24 hours at 65° to 75° F. and then placed into a controlled temperature room. Treatment evaluations were made 7 to 8 days after inoculation. The results are reported in Table III as the percent disease control and represent the level of disease suppression when compared to the untreated control plants present at spraying and inoculation that was dark green, not yellow, compared to the untreated control leaves.

(b) Tomato Late Blight (TLB)

*Phytophthora infestans* was maintained on 6 to 8 inch tall Rutgers tomato seedlings for 4 to 5 days in a constant temperature humidity chamber at 65° to 75° F. with moderate light intensity. A water suspension of the spores from infested plants was obtained and the spore concentration was adjusted to about $1 \times 10^5$ spores/ml.

Rutgers tomato seedlings, 3 to 5 inches tall, were fertilized with a water-soluble fertilizer to promote rapid succulent growth. About 4 to 5 days later, the seedlings were sprayed to runoff with a solution of a test compound comprising 300 ppm of the active ingredient of the test compound in a 2:1:1 mixture of water, acetone and methanol. After drying, the tomato late blight spore suspension was applied to the lower left surface of the plant leaves with a DeVilbiss atomizer until fine droplets were visible on the leaves. The inoculated seedlings were placed in a humidity cabinet at 65° to 70° F. for 24 hours and then moved to a controlled temperature humidity chamber until treatment evaluations were made about 5 to 7 days after inoculation. The results are reported in Table III as percent disease control which represents the percentage of the treated plants (leaves and stems) lacking of disease signs or symptoms where compared to untreated control plants.

(c) In Vitro Tests

In vitro testing was done to determine the effects of the test compounds on the mycelial growth of *Pythium ultimum* and *Phytophthora capsici*. Corn meal agar was autoclaved for 15 minutes and agar suspensions containing a concentration of each test compound at 100 ppm (based on weight to weight). The agar was poured into petri dishes and allowed to harden. Thereafter, 6 mm circular mycelial fungal plugs of 1 week old stock culture grown on amended corn meal agar were placed on the surface of the agar in the petri dishes. The dishes were incubated under light at room temperature, about 22° C., for two days (*P. ultimum*) and three days (*P. capsici*) until the colonies in the control dishes had grown about half or more of the diameter of the petri dish. The control dishes consisted of corn meal agar amended with 2 ml of acetone, the solvent used for the test compounds. The diameter (mm) of the mycelial growth in each dish was measured. The results are reported in Table III as percent growth inhibition calculated from the measured colony diameters of the control colonies and colonies grown in the presence of test compounds as follows:

$$\text{Percent Growth Inhibition} = \frac{\text{Dia. of Control Growth (mm)} - \text{Dia. of Test Cpd. Growth(mm)}}{\text{Diameter Control Growth (mm)}} \times 100$$

TABLE 3

| | Fungicidal Activity | | | |
|---|---|---|---|---|
| Example | CDM | TLB | *P. ultimum* | *P. capsisi* |
| 1 | 100 | 100 | 100 | 100 |
| 2 | 100 | 100 | 100 | 100 |
| 3 | 100 | 50 | 100 | 100 |
| 4 | 80 | 60 | 100 | 100 |
| 5 | 100 | 40 | 100 | 100 |
| 6 | 100 | 100 | 100 | 70 |
| 7 | 100 | 90 | 100 | 100 |
| 8 | 100 | 70 | 100 | 100 |
| 9 | 100 | 40 | 100 | 100 |
| 10 | 80 | 20 | 100 | 60 |
| 11 | 20 | 20 | 80 | 30 |
| 12 | 100 | 100 | 100 | 100 |
| 13 | 100 | 50 | 100 | 100 |
| 14 | 100 | 100 | 100 | 50 |
| 15 | 100 | 100 | 100 | 100 |
| 16 | 100 | 70 | — | — |
| 17 | 100 | 80 | 100 | 90 |
| 18 | 100 | 100 | 100 | 100 |
| 19 | 100 | 100 | 100 | 100 |
| 20 | 100 | 100 | 100 | 100 |
| 21 | 0 | 0 | — | — |

It is to be understood that changes and variations may be made without departing from the spirit and scope of the invention as defined by the appended claims.

What is claimed is:

1. A compound of the formula

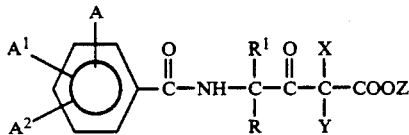

(I)

wherein

A, $A^1$ and $A^2$ are each independently selected from hydrogen, halogen, ($C_1$-$C_4$)alkyl, halo($C_1$-$C_3$)alkyl, ($C_1$-$C_4$)alkoxy, halo($C_1$-$C_3$)alkoxy, cyano, nitro, phenyl, phenyl($C_1$-$C_3$)alkyl or phenyloxy;

R and $R^1$ are each independently selected from hydrogen, ($C_1$-$C_6$)alkyl, phenyl, phenyl($C_1$-$C_4$)alkyl and halo($C_1$-$C_3$)alkyl;

X is halogen, cyano or thiocyano (—SCN);

Y is hydrogen, halogen, cyano or thiocyano (—SCN); and Z is hydrogen, ($C_1$ - $C_8$) alkyl, ($C_1$-$C_3$) alkoxy($C_1$-$C_3$) alkyl, halo($C_1$-$C_8$)alkyl, phenyl, phenyl($C_1$-$C_4$)alkyl, phenoxy($C_1$-$C_4$)alkyl, ($C_1$-$C_4$) alkoxycarbonyl($C_1$-$C_4$) alkyl, acyl(-$C_1$-$C_6$)alkyl or thio($C_1$-$C_8$)alkyl; and its agronomically acceptable salts.

2. The compound of claim 1 wherein A is hydrogen, chloro, bromo, fluoro, iodo, trifluoromethyl, trifluoromethoxy, methyl, ethyl, phenyl, methoxy, chloromethyl or cyano; $A^1$ and $A^2$ are each independently selected from hydrogen, chloro, bromo, fluoro, and methyl groups; R and $R^1$ are hydrogen, ($C_1$-$C_6$)alkyl or phen($C_1$-$C_2$)alkyl; X is fluoro, chloro, bromo or thiocyano; Y is hydrogen, fluoro, chloro, bromo or thiocyano; and Z is H, ($C_1$-$C_5$)alkyl, halo($C_1$-$C_5$)alkyl having from 2 to 6 halogens, phenyl, ($C_1$-$C_3$)alkoxy($C_1$-$C_3$)alkyl, ($C_1$-$C_3$)alkoxycarbonyl($C_1$-$C_3$)alkyl, or phenyl($C_2$-$C_4$)alkyl and its agronomically acceptable salts.

3. The compound of claim 2 wherein A, $A^1$ and $A^2$ are at the 3-, 4- or 5-position of the phenyl ring; A is chloro, bromo, trifluoromethyl, fluoro or methyl; $A^1$ and $A^2$ are each independently selected from hydrogen, chloro, bromo and fluoro; R and $R^1$ are each independently ($C_1$-$C_4$)alkyl; X is bromo or chloro; Y is hydrogen, fluoro, chloro or bromo; and Z is hydrogen, ($C_1$-$C_3$)alkyl, halo($C_2$-$C_4$)alkyl having from 1 to 4 halogens, phenyl, halophenyl, ($C_1$-$C_3$)alkoxy($C_1$-$C_3$)alkyl, or ($C_1$-$C_3$)alkoxycarbonyl($C_1$-$C_3$)alkyl.

4. The compound of claim 3 wherein A, $A^1$ and $A^2$ are at the 3-, 4- and 5-positions respectively of the phenyl ring; A is chloro, bromo, fluoro, trifluoromethyl or methyl group; $A^1$ is hydrogen; $A^2$ is hydrogen, chloro, bromo or fluoro; R and $R^1$ are each independently ($C_1$-$C_2$)alkyl; X is bromo or chloro; Y is hydrogen or chloro; and Z is methyl, ethyl, isopropyl, chloroethyl, chlorophenyl, methoxyethyl or ethoxycarboxylmethyl.

5. The compound of claim 4 wherein A is chloro; $A^1$ is hydrogen; $A^2$ is chloro or hydrogen; R is methyl or ethyl; $R^1$ is methyl; X is bromo or chloro; Y is hydrogen or chloro; and Z is hydrogen, methyl, ethyl, isopropyl, 2-chloroethyl, 4-chlorophenyl, methoxyethyl, ethoxycarbonylmethyl or sodium.

6. The compound of claim 5 wherein $A^2$ is chloro, R is methyl, X is chloro, and Z is methyl, ethyl, 4-chlorophenyl, hydrogen, 2-chloroethyl, methoxyethyl or ethoxycarbonylmethyl.

7. The compound of claim 5 wherein $A^2$ is chloro, R is methyl, X is bromo and Z is hydrogen, methyl, ethyl, 4-chlorophenyl or sodium.

8. The compound of claim 5 wherein $A^2$ is chloro, R is ethyl, X is chloro and Z is hydrogen or methyl.

9. The compound of claim 5 wherein $A^2$ is chloro, R is ethyl, X is bromo and Z is hydrogen or methyl.

10. The compound of claim 5 wherein the compound is 2-chloro-4-(3-chlorobenzoylamino)-4-methyl-3-oxohexanoic acid, methyl ester; 2,2-dichloro-4-(3,5-dichlorobenzoylamino)-4-methyl-3-oxohexanoic acid, methyl ester; or 2-bromo-4-(3-chlorobenzoylamino)-4-methyl-3-oxohexanoic acid.

11. A fungicidal composition which comprises an agronomically acceptable carrier and a fungicidally-effective amount of the compound of claim 1.

12. A fungicidal composition which comprises an agronomically acceptable carrier and a fungicidally-effective amount of the compound of claim 5.

13. A method for controlling phytopathogenic fungus which comprises applying to the fungus or its habitat a fungicidally-effective amount of the compound of claim 1.

14. A method for controlling phytopathogenic fungus which comprises applying to the fungus or its habitat a fungicidally-effective amount of the compound of claim 5.

* * * * *